United States Patent
Ong et al.

(10) Patent No.: US 7,098,256 B2
(45) Date of Patent: Aug. 29, 2006

(54) ANTIMICROBIAL RADIATION CURABLE COATING

(75) Inventors: Ivan W. Ong, Charlotte, NC (US); Robert S. Watterson, deceased, late of Charlotte, NC (US); by Julia M. Watterson, legal representative, Fort Myers, FL (US); C. Barry Wilson, Charlotte, NC (US)

(73) Assignee: Microban Products Company, Huntersville, NC (US)

( * ) Notice: Subject to any disclaimer, the term of this patent is extended or adjusted under 35 U.S.C. 154(b) by 0 days.

(21) Appl. No.: 10/492,008

(22) PCT Filed: Oct. 9, 2002
(Under 37 CFR 1.47)

(86) PCT No.: PCT/US02/32228

§ 371 (c)(1),
(2), (4) Date: Jul. 8, 2004

(87) PCT Pub. No.: WO03/054045

PCT Pub. Date: Jul. 3, 2003

(65) Prior Publication Data

US 2005/0080158 A1  Apr. 14, 2005

Related U.S. Application Data

(60) Provisional application No. 60/328,202, filed on Oct. 10, 2001.

(51) Int. Cl.
  *C08F 2/46*   (2006.01)
  *B32B 27/40*  (2006.01)
  *B32B 27/38*  (2006.01)

(52) U.S. Cl. ............ 522/97; 522/93; 522/96; 522/90; 522/100; 522/71; 522/74; 522/78; 522/79; 522/81; 428/423.1; 428/413

(58) Field of Classification Search .......... 522/97, 522/93, 100, 71, 74, 78, 79, 81, 83; 428/413, 428/423.1
See application file for complete search history.

(56) References Cited

U.S. PATENT DOCUMENTS

| | | | |
|---|---|---|---|
| 5,003,026 A | 3/1991 | Ehrhart et al. | |
| 5,135,964 A | * 8/1992 | Lee et al. | 522/96 |
| 6,102,205 A | * 8/2000 | Greff et al. | 206/438 |
| 6,242,506 B1 | 6/2001 | Fan et al. | |
| 6,399,670 B1 | 6/2002 | MacQueen et al. | |
| 6,399,672 B1 | 6/2002 | Ceska et al. | |
| 6,423,381 B1 | 7/2002 | Colton et al. | |
| 6,730,388 B1 | 5/2004 | MacQueen et al. | |
| 6,790,512 B1 | 9/2004 | MacQueen et al. | |
| 2005/0009943 A1 | 1/2005 | MacQueen et al. | |

FOREIGN PATENT DOCUMENTS

WO  WO97/46627  12/1997

OTHER PUBLICATIONS

Sartomer (Exton, PA), "Urethane Acrylate Oligomers", Product Bulletin, date unknown, 14 pages, Exton, PA.

* cited by examiner

*Primary Examiner*—Sanza L. McClendon
(74) *Attorney, Agent, or Firm*—Cliff D. Weston

(57) ABSTRACT

The invention is a radiation curable coating containing an antimicrobial agent, where upon irradiation with UV light, the radiation curable coating rapidly cures to a polymeric coating. The polymeric coating has durable antimicrobial properties, being especially effective at preventing the growth of *Staphylococcus aureaus* and *Kleibsella pneumoniae* on wood flooring and furniture. The major components in the radiation curable coating are a urethane acrylic oligomer, a radiation cure package, an antimicrobial agent, a cross-linking agent, and optionally, an additive package. The radiation curable urethane oligomer is a relatively short chain backbone urethane polymer that is end capped with a radiation curable moiety, where the moiety is an acrylic. The cross-linking agent is one or more monomers used to lower the viscosity and promote cross-linking, and include acrylate esters of mono-, di-, tri-, or tetrafunctional alcohols. The radiation cure package contains at least one photoinitiator.

13 Claims, No Drawings

ANTIMICROBIAL RADIATION CURABLE COATING

CROSS REFERENCE TO RELATED APPLICATION

This application claims the benefit of the prior filing date of U.S. Provisional Patent Application No. 60/328,202, which was filed on Oct. 10, 2001.

FIELD OF THE INVENTION

This invention relates generally to polymeric coatings having antimicrobial properties, and more particularly to radiation cured coatings having antimicrobial properties.

BACKGROUND OF THE INVENTION

Polyurethanes are widely used to provide a durable coating on numerous consumer products requiring abrasion resistance, flexibility, and chemical resistance. Polyurethane coating systems are typically fast curing, have good adhesion to a wide variety of substrates, good leveling properties and are excellent film formers. Polyurethane-type coatings may be applied as clear coats with generally transparent or translucent characteristics, thereby making polyurethane coatings ideal for many different applications and, particularly, to enhance and protect the appearance of products, for instance wood paneling and as furniture. Also, polyurethane coatings may be colored to produce coatings that when properly formulated, have good color fastness, while still providing the qualities of substantial abrasion resistance and chemical resistance. Because of their excellent adhesion, polyurethane coatings are often applied directly to the surface of the product, and do not require a primer coat. Many urethane coatings are applied as reactive oligomers, wherein the oligomers are prepolymers that have unreacted isocyanate groups; Typically, prepolymers are reduced or diluted in an aprotic solvent such as an aromatic solvent (i.e. toluene), a ketone (i.e. methyl ethyl ketone), an ester (i.e. butyl acetate), an ether (i.e. tetrahydrofuran), a tertiary amine (i.e. 1-methyl pyrrolidone), or a mixture thereof. Potentially the isocyanate group can react with the substrate, react with ambient moisture, or with an in situ reactant, forming a cross-linked polymer with excellent abrasion resistance. Most urethane coatings applied to wood or simulated wood surfaces cure through reaction with the ambient moisture. The major advantage of a moisture curing system is that the coating has a long pot life. A potential disadvantage is that the isocyanate group can react with additives in the coating having labile protons (i.e. alcohols, carboxylic acids and most amines). Another disadvantage to moisture-cured urethanes is that the cure time of the coating can vary significantly depending on the ambient conditions, and this uncertainty makes it difficult to execute a production schedule. Variable cure times can also affect how much of the coating remains on the surfaces of the substrate, and can necessitate in an additional coating. The major disadvantage to urethane oligomers is that they cure through an isocyanate functional group, and airborne isocyanates are extremely toxic. Typical exposure limits (TLV) are in the parts per billion range, and heated air ovens generally create air borne isocyanates which must be environmentally treated.

A preferable coating is one that has a long pot life, yet could be cured to a highly cross-linked state virtually instantaneously. It would be further preferable if the coating could be cured with very little heat. A further preference is that the coating can be applied at very high solids, with a target of 100% solids, so as to eliminate the removal and disposal of solvent. A most important consideration is that the coatings not cure through an isocyanate group, but via another moiety that is lower in toxicity.

Wood surfaces, such as hardwood flooring, furniture used in office, residential, health care and hospitality environments, and cabinetry are ideally suited for coating with polyurethanes in order to protect the surfaces from abrasion and to provide chemical resistance. Furthermore, synthetic or natural surfaces and ceramics can be enhanced by such a coating.

Furniture and other wood products are under constant exposure to bacteria, fungi and microbes that exist in their respective environments. For example, polyurethane coated flooring, cabinetry, and furniture are particularly susceptible to bacteriological and other microbial development. People and moveable objects, both of which are carriers of bacteria and microbes, account for the majority of microbes on the flooring of heavily trafficked areas. The traffic results in a continual deposit of bacteria and microbes on the floorings, and consequently there develops a "bioburden" which is a continuous source for cross-contamination. Additionally, polyurethane coated cabinetry and surfaces found in bathrooms and kitchens, whether incorporated in domestic settings or commercial settings, produce a bioburden as a consequence of being in contact with contaminated parts of the body. Residual microbes typically remain and continue to populate the coated flooring, cabinetry, furniture, and other surfaces.

The net effect is that there are created a variety of environments which are a constant source of bacterial, fungal or other microbial contamination. Not only are polyurethane coated products contaminated by the bacteria, fungi and microbes in these environments, but these environments also aid in the proliferation of the bacteria, fungi and microbes. The presence of humidity or moisture in these environments is generally conducive to the growth of bacteria, fungi and microbes. Bacteria, fungi and microbes can grow and multiply on the surfaces of the coated products, producing significant levels of contamination, in the form of a bioburden. If left unchecked, the bioburden builds over time.

To counter the presence and growth of microbes on the surface of polyurethane coated products, a disinfectant or sanitizing agent is typically applied to the surface, such as by washing, spraying or wiping. Unfortunately, disinfectants and sanitizing agents are not always properly applied and thus not always completely effective. In any case, topically applied disinfectants and sanitizing agents provide only temporary removal of the microbes on the surface because, as previously mentioned, the associated environment is a source for further contamination. Reapplication of the disinfectant and sanitizing agent is costly, time consuming, non-durable, and therefore only temporarily controls the presence and growth of microbes.

Furthermore, non-thorough cleaning of the polyurethane coated products leaves residual contamination as previously mentioned. Without attention to detail when cleaning the coated products, residual contamination is more likely to exist. Additionally, by applying the disinfectant or other biocide to the surface of the coated product, a residual of the disinfectant or biocide enters the environment and may negatively impact the environment.

What is needed is an antimicrobial agent that can be incorporated, or embedded, into a polymeric coating prior to polymerization, where that antimicrobial agent survives polymerization. In particular, what is needed is an antimicrobial agent incorporated into a polymeric coating that is applied to surfaces, and that is free from toxic effects and is durable over the lifespan of the polymer coating. Further needed is a polymeric coating having at least one antimicrobial agent incorporated in the polymeric coating where the antimicrobial agent will migrate to the surface of the polymeric coating as needed to provide appropriate protection. Further needed is a polymeric coating having antimicrobial properties that may be applied by conventional coating techniques. Further needed is a polymeric coating having antimicrobial compounds or chemicals incorporated in the polymeric coating, wherein the addition of the antimicrobial compounds or chemicals has no deleterious effect on the properties of the coating, so that the mechanical and physical properties remain unaffected.

And further still, it is desired that the coating be applied at substantially 100% solids, and that the coating is a urethane coating or a similar coating having durable antimicrobial properties with good efficacy.

There have been some reported successes in medicinal chemistry of the preparation of antimicrobial film coatings using urethane acrylates in combination with antimicrobial agents. Greff et al., U.S. Pat. No. 6,102,205 discloses a polyvinylpyrrolidone iodine complex (e.g. PVP-$I_2$), which is admixed with a urethane acrylate prepolymer and a photoinitiator system that initiates polymerization in visible light, forming an antimicrobially effective film. The antimicrobially effective film is biocompatible with mammalian skin.

There is some prior art concerned with flooring and other wood or simulated wood surfaces utilizing radiation curable urethane acrylates, such as Ehrhart et al, U.S. Pat. No. 5,003,026, but these coatings are substantially concerned with gloss, wear and stain resistance. Erhart'026 discloses several urethane acrylate oligomers that are suitable for wood coating.

A major manufacturer of urethane acrylic oligomers is Sartomer Technologies Co, Inc., of Exton Pa., and inventors Ceska et al., U.S. Pat. No. 6,399,672, discloses radiation curable coating compositions, where the compositions can be formulated to cure by microwave, UV or electron beam radiation. These forms of radiation are also known to have sterilization properties, and Ceska'672 notes that coatings cured using this technology would be useful for flooring and can (as in canned goods) coatings. Ceska'672 does not teach the utility of adding antimicrobial agents.

Berg et al., U.S. Pat. No. 6,096,383, discloses a process for applying a coating to a floor surface and curing that coating with UV radiation. The source of UV radiation is mounted on the front of a self-powered vehicle.

SUMMARY OF THE INVENTION

The present invention is a radiation curable polymeric coating with an antimicrobial agent. The radiation curable coating comprises a radiation cross-linkable oligomer, a radiation cure package, an antimicrobial agent, a cross-linking agent, and optionally, an additive package. The radiation cross-linkable oligomer is a short chain, preferably liquid, that is end capped with a reactive moiety, consisting of the group of adducts selected from acrylates, methacrylates, allylic radicals or epoxies, where the adducts are susceptible to radiation cross-linking. The UV radiation cross-linkable oligomers of the invention are typically urethane acrylates and urethane methacrylates, where, hereinafter, are jointly referred to as urethane acrylate oligomers.

The urethane acrylate oligomers are the reaction products of a hydroxy-containing acrylate ester, usually 2-hydroxy ethyl acrylate or hydroxy propyl acrylate with an isocyanate prepolymer. The isocyanate prepolymer is typically a polyether or a polyester prepolymer, formed as the reaction product of di- and tri-functional polyols (ethylene, propylene, 1,2-butylene, isobutylene oxide) or ethers (tetrahydrofuran) and isocyanates. Other suitable polyols include for example ethoxylated polypropylene glycols, polybutylene and isobutylene diols and triols, and ethoxylated or propoxylated glycerol or ethoxylated or propoxylated glycerol or ethoxylated or propoxylated trimethylol propane or trimethylol ethane. Examples of polyesters suitable for forming isocyanate prepolymers include polycaprolactones, aliphatic and aromatic di- and tri-polyesters terminating in a hydroxy moiety. Suitable isocyanates are di or polyisocyanates, and include the aromatic isocyanates such as toluene di-isocyanate or di-phenyl methane di-isocyanate, aromatic diisocyanates such as tetramethyl xylylene di-isocyanate, and aliphatic or cycloaliphatic di-isocyanates such as isophorone-di-isocyanate, bis-isocyanate cyclohexyl methane, hexa-methylene di-isocyanates and alkyl substituted hexa-methylene di-isocyanates.

Urethane acrylic oligomers generally cure via a free radical mechanism and epoxy urethane oligomers cure by a cationic mechanism, and the photoinitiator is suitably selected to generate the requisite free radical or cation, respectively.

The radiation cure package is one or more initiators selected to be responsive to the type of radiation. For instance, UV radiation requires a primary photoinitiator, and optionally an accelerator and a secondary photoinitiator. The cross-linking agents are one or more compounds that have at least two radiation cross-linkable moieties, such as acrylate, methacrylate, or epoxy, and frequently have three or more moieties. The additive package includes diluents, plasticizers, antioxidants, colorants, solvents, emulsifiers, water and fillers. The antimicrobial agent is non-toxic and free of heavy metals and may be organic, inorganic, or organometallic. The antimicrobial agent is selected from conventional organic or organometallic antimicrobial substances such as halogenated phenyl ethers, halogenated salicylanilides, sesquiterpene alcohols, halogenated carbanilides, bisphenolic compounds, general phenols, formaldehyde, quaternary ammonium compounds, pyridine derivatives and hexachlorophene. Many of the coatings are clear, and disinfectants such as iodine, and complexes thereof, are highly colored and are unsuitable for the instant invention. Also useful are inorganic antimicrobials utilizing silver, zinc, or copper in glass or ceramic matrices. The antimicrobial agent is preferably 2,4,4'-trichloro-2'-hydroxydiphenyl ether.

In a typical embodiment, the radiation curable coating is coated onto the substrate (i.e. furniture), and then cured via exposure to a UV light.

The incorporated antimicrobial agent inhibits bacterial, fungal, microbial and other pathogen or non-pathogen growth and migrates to the coated surface as required, thereby establishing a concentration gradient that controls the growth of microorganisms on contact with the coated surface. This technology provides antimicrobial characteristics to surfaces, specifically wood surfaces, such as hardwood flooring, furniture (office, residential, health care, and hospitality), and cabinetry. By treating the radiation curable coating with an antimicrobial additive, such as MICROBAN® Additive B (e.g. Triclosan) the cured coating is resistant to growth and formation of microbes. The antimicrobial agent is not destroyed during the radiation curing, which is somewhat surprising in light of its sensitivity to radiation, and particularly to UV light. The incorporated antimicrobial agent is durable over the lifespan of the polymer coating. Radiation curable coatings have a relatively high cross-link density, and the invention has unanticipated efficacy for a polymer coating with a tight cross-linking network. Previous investigations of incorporating an antimicrobial agent in a polymer have seen a significant reduction in efficacy as the cross-linking increased. Presumably, the drop in efficacy is because the antimicrobial cannot move through the coating. However, in light of the unexpected efficacy, the hypothesized mechanism should be reviewed for radiation-cured polymers, and particularly for polyurethane acrylic polymer systems.

The invention is particularly suitable for coating flooring, furniture, cabinetry and other products that are susceptible to bacterial/microbial contamination.

The present invention provides more hygienic living and working environments in settings where manufactured and natural materials are found. Incorporation of the present invention on surfaces in health care and food service facilities where bacteria and bioburdens pose a health hazard is especially beneficial. Additionally, use of antimicrobial agents in a protective polymer coating protects the surface of the coating from attack by bacterial, fungal, or other microbial contamination. This internal protection makes the coating more durable and long lasting.

The cross-linking agents that are added to the UV curable antimicrobial coatings typically are monomers which are blended with the above urethane oligomers in order to yield a composition having good coating properties and an acceptable rate of cure. Monomers are used to lower the viscosity and promote cross-linking, and are frequently referred to as diluents. Examples of monomers include acrylate esters of mono-, di-, tri-, and tetrafunctional alcohols. Commonly used materials include glycerol triacrylate, trimethylol propane triacrylate, trimethylol ethane triacrylate, pentaerythritol tetracrylate, together with the acrylates of the ethoxylates or propoxylates of the above alcohols. Difunctional monomers consist usually of the acrylate esters of ethylene glycol or propylene glycol and their oligomers, with tripropylene glycol diacrylate being especially preferred, diacrylates of longer chain alcohols such as hexanediol diacrylate and acrylate esters of cycloaliphatic diols such as the cyclohexane diols. Monofunctional monomers consist of the acrylate esters of mono functional alcohols such as octanol, nonanol, decanol, dodecanol, tridecanol and hexadecanol both in their linear and branch chain forms. Also included are cyclohexyl acrylate and its alkyl derivatives such as t-butylcyclohexyl acrylate and tetrahydrofurfuryl acrylate. N-vinylpyrrolidone has also been used as a monofunctional monomer. The weight percent of the composition of the curable coating comprised of the monomer is limited by the attendant shrinkage on curing, which can cause the resulting polymeric coating to exhibit skin effects, such as alligatoring, wherein the polymeric coating has wrinkles.

In general, high functionality monomers give rapid cure speeds and high cross-link density, leading to films of high hardness and tensile strength with excellent chemical resistance. Monofunctional monomers, conversely, give slow cure speeds and low cross-link density, leading to cured films of lower hardness, tensile strength, and with reduced chemical resistance. These properties can be influenced by the presence of transfer agents, which tend to produce-lower cross-link density, and slower gelling compositions, which can result in a more complete cure. The cure is also affected by the thickness of the coating, the presence of oxygen, the presence of preservative antioxidants (i.e. BHT, hydroquinone, and similar compounds) that are added to prevent premature curing, the intensity of the UV light and the level of IR light.

OBJECTS OF THE INVENTION

The principal object of the invention is to provide a polymeric coating having antimicrobial protection incorporated in the radiation curable coating that may be applied to solid surfaces.

Another, more particular object of the invention, is to provide a polymeric coating for surfaces having antimicrobial protection incorporated in the polymer coating in a cost-effective, non-toxic and durable way.

Another object of the invention is to provide a cured polymeric coating that has antimicrobial agents incorporated therein, in which the surface of the coating reflects antimicrobial efficacy consistent with the controlled migration of the antimicrobial agent to the surface of the polymeric coating.

Another object of the invention is to provide a polymeric coating having antimicrobial compounds or chemicals incorporated in the coating, wherein the coating has physical, mechanical and surface appearance characteristics comparable to a polyurethane coating.

Another object of the invention is to provide a radiation curable coating for surfaces in which there is no discoloration of the coated surface, and the activity and efficacy of the antimicrobial agent is not depleted over the life of the coating.

Another object of the invention is to provide a radiation curable coating wherein, if the agent is depleted from the surface of the coating by abrasion or by chemical means (i.e. a cleaning agent), then the antimicrobial agent will migrate to the surface, therein regenerating the antimicrobial efficacy.

Another object of the invention is to provide a radiation curable coating in which an antimicrobial agent protects the polymeric coating and the coated surface from attack by bacterial, fungal, or other microbial contamination, providing improved longevity to the coating.

Another, more particular object of the invention is to provide a radiation curable coating for surfaces having an antimicrobial compound incorporated in the polymeric coating that does not exhibit sublimation of the antimicrobial compound at ambient temperatures.

Another object of the invention is to provide a urethane acrylic curable coating that is cured by radiation, and particularly UV, wherein the urethane acrylic curable coating is free of isocyanate groups.

Another object of the invention is to provide a radiation curable coating that can be applied at very high solids, and can be cured within a matter of seconds using radiation. Examples of radiation include UV light, visible light, and electron beam radiation.

DETAILED DESCRIPTION OF THE INVENTION

The present invention is a radiation curable coating containing an antimicrobial agent, where upon irradiation with UV light the curable coating rapidly cures to a polymeric coating having durable antimicrobial properties. The polymeric coating has good adhesion to wood and simulated wood surfaces. The radiation curable coating comprises a urethane acrylic oligomer, a radiation cure package, an antimicrobial agent, a cross-linking agent, and optionally, an additive package. The radiation curable urethane oligomer is a relatively short chain backbone urethane polymer that is end capped with a radiation curable moiety, where the moiety is an acrylic, a methacrylic, an allylic or an epoxy adduct or a combination thereof. The urethane acrylic oligomer preferably is a liquid at room temperature. There are substantially no remaining isocyanate groups on the oligomer, therein neutralizing environmental issues surrounding the use of isocyanates. The radiation cure package is one or more initiators selected to be responsive to the type of radiation. For instance, UV radiation requires a primary photoinitiator, and optionally, an accelerator and a secondary photoinitiator. The cross-linking agent is a compound that has at least two radiation curable functional groups, wherein the functional groups are selected from the radiation curable moieties consisting of acrylic, methacrylic, epoxy, allyl and vinyl functional groups. The cross-linking agent frequently has three or more functional groups, and not infrequently, the cross-linking agent also serves as a diluent for reducing the viscosity of the radiation curable coating. The urethane acrylic oligomer is typically too viscous to be coated without further compounding. The additive package can include other diluents, plasticizers, antioxidants, colorants, solvents, emulsifiers, water, leveling agents, wetting agents, micro balloons, glass and phenolic beads, and fillers. The preferred antimicrobial agent is 2,4,4'-trichloro-2'-hydroxydiphenyl ether. In the preferred embodiment, the radiation curable coating is coated onto the substrate (i.e. furniture, wood flooring), and then cured via exposure to a UV light source of radiation. Examples of suppliers of UV light sources are Fusion Systems and Hanovia Ltd based in Slough, England. The UV light source is typically a mercury based lamp, where the mercury is excited using either electrodes or the lamp is electrode less and the mercury vapor is excited using microwave radiation. Often the lamp is doped to shift the frequency to a spectral region where the photoinitiator has a strong absorption. Medium pressure mercury are the typically a preferred source. Newer lamps, including iron, indium, gallium and metal halide lamps have been developed, and their application is anticipated.

The radiation curable coating is applied to wood or simulated wood surfaces using conventional coating methods (i.e. by coating, spraying, pouring and brushing). An effective amount of the antimicrobial agent (e.g. 2,4,4'-trichloro-2'-hydroxydiphenyl ether) is from about 0.075% to about 3% by weight of the polymeric coating.

Additionally, silver based or other metal oxidizing antimicrobial agents may also be used. An alternative antimicrobial agent is polyhexamethylene biguanide hydrochloride (PHMB). Other chemical compounds having known antimicrobial characteristics may also be used in the present invention.

The polymeric coating is substantially a urethane acrylic polymer having the antimicrobial agent incorporated therein. The polymeric coating is durably resistant to the growth of fungus, yeast, and gram positive and gram-negative bacteria including *Staphylococcus aureus, Kleibsella pneumoniae* and *Salmonella*.

The efficacy of the antimicrobial polymeric coating was determined through a series of trials using different coating thickness and at various concentrations of the antimicrobial agent. A summary of the efficacy studies follows.

The radiation curable coating is coated onto wood flooring panels. The curable coating is irradiated with UV light. The antimicrobial efficacy of the resulting polymeric coating is measured using the Kirby Bauer Test Method. Following the Kirby Bauer test procedure, 20 mm square samples of the coated wood flooring panel are cut from the coated flooring panels, and a single sample is placed into a petri dish containing Mueller-Hinton Agar. The individual petri dishes are inoculated with a bacterium. The various perturbations in the petri dishes are incubated at 37° C.±2° C. for 18–24 hours. The coating thickness is varied from about 5 microns to about 13 microns, and the concentration of the antimicrobial from 0 wt. % to about 3 wt. % of the weight of the radiation curable coating. The results for the antimicrobial, triclosan, are given in Table 1. The Control contains no antimicrobial agent. The polymeric coating was tested for efficacy at inhibiting the growth of *Staphylococcus aureus* (ATCC 6538), and *Kleibsella pneumoniae* (ATCC 4352).

TABLE 1

| SAMPLE IDENTIFICATION | RESULTS (ZONE SIZE) | |
|---|---|---|
| ID, Coating Thickness, % Antimicrobial | S. aureus | K. pneumoniae |
| Control, 5.1 micron coating, 0% triclosan | NZ/NI | NZ/NI |
| Control, 12.7 micron coating, 0% triclosan | NZ/NI | NZ/NI |
| 7608, 5.1 micron coating, 0.5% triclosan | 1 mm | NZ/NI |
| 7609, 12.7 micron coating, 0.5% triclosan | NZ/NI | NZ/NI |
| 7610, 5.1 micron coating, 1.0% triclosan | 1 mm | 1 mm |
| 7611, 12.7 micron coating, 1.0% triclosan | 1 mm | 1 mm |
| 7612, 5.1 micron coating, 2.0% triclosan | 2 mm | 3 mm |
| 7613, 12.7 micron coating, 2.0% triclosan | 4 mm | 4 mm |
| 7614, 5.1 micron coating, 3.0% triclosan | 4 mm | 4 mm |
| 7615, 12.7 micron coating, 3.0% triclosan | 4 mm | 3 mm |

These batteries of tests clearly demonstrate, as evidenced by comparison with the Control, that without the antimicrobial agent there is "no zone of inhibition" (NZ) surrounding the sample, and that there is "no inhibition" (NI) of growth under the sample. The zone of "inhibition" (I) of growth is reported in millimeters (mm). The antimicrobial agent becomes effective at a concentration between about 0.5% and about 1.0%. Effectiveness is not substantially increased as the concentration approaches about 3%, as the zone of inhibition is not continuing to increase. The efficacy appears to be independent of the coating thickness. A coating thickness of 5.1 microns substantially produces the same level of inhibition as a 12.7 micron thickness. For instance, compare sample 7612 against 7613, and 7614 against 7615.

Quantitative testing (AATC Test Method 100-1993) of radiation cured coatings with and without triclosan demonstrated that at even low concentrations the antimicrobial coating affects the growth rate of *Staphylococcus aureus* and *Kleibsella pneumoniae*. A control test strip having a radiation cured coating of approximately 5.1 microns thick, and a sample test strip having a radiation cured coating with 1500 ppm weight percent (0.15%) of triclosan were immersed in inoculated nutrient agar and incubated for 18–24 at 37° C.±2° C. After 24 hours the *Staphylococcus aureus* had increased 524% for the control and only 116% for the coating containing triclosan. The *Kleibsella pneumoniae* had increased 6334% for the control and only 320% for the coating containing triclosan. At even relatively low levels of antimicrobial agent, the radiation cured coating retarded growth of both *Staphylococcus aureus* and *Kleibsella pneumoniae*.

SUMMARY OF THE ACHIEVEMENT OF THE OBJECTS OF THE INVENTION

It is readily apparent that we have invented a radiation curable coating for surfaces having antimicrobial protection incorporated in the cured coating. The present invention provides a polymeric coating comprised of a cross-linked urethane acrylic polymer having antimicrobial protection incorporated in the coating. The radiation curable coating is suitable for application to wood and simulated wood surfaces. The present invention provides durable antimicrobial protection to the surface of wood substrates that historically have used polyurethane coatings and lacquers that do not provide antimicrobial protection.

It is to be understood that the foregoing description and specific embodiments are merely illustrative of the best mode of the invention and the principles thereof, and that various modifications and additions may be made to the apparatus by those skilled in the art, without departing from the spirit and scope of this invention.

What is claimed is:

1. A radiation curable coating having antimicrobial properties, comprising:
    a radiation curable urethane oligomer having an epoxy functionality;
    a radiation cure package;
    a cross-linking agent; and
    at least one antimicrobial agent;
    whereby, upon curing, the radiation curable coating forms a polymeric coating that exhibits unanticipated high antimicrobial efficacy.

2. The radiation curable coating as claimed in claim 1, wherein said antimicrobial agent is at least one of 2,4,4' trichloro-2'-hydroxydiphenyl ether, zinc pyrithione, silver, zinc, or copper in zeolite matrix, para-chloro-xylene, hexachlorophene.

3. The radiation curable coating as claimed in claim 1, wherein said radiation cure package contains a UV photoinitiator.

4. The radiation curable coating as claimed in claim 1, wherein said antimicrobial agent is present in a concentration of from about 0.075% to about 5% by weight of the polymeric coating.

5. The radiation curable coating as claimed in claim 1, wherein said polymeric coating has a zone of growth inhibition of *Staphylococcus aureus* and *Kleibsella pneumoniae*.

6. The radiation curable coating claimed in claim 1, wherein said cross-linking agent is one or more monomers which include acrylate esters of mono-, di-, tri-, or tetrafunctional alcohols, and which lower the viscosity and promote cross-linking.

7. The radiation curable coating claimed in claim 3, where said radiation curable coating is curable upon radiation with UV light.

8. An article coated with the antimicrobial radiation curable coating of claim 1.

9. The article coated with a radiation curable coating having antimicrobial properties as claimed in claim 8, wherein said article is made of wood.

10. The article coated with a radiation curable coating having antimicrobial properties as claimed in claim 8, wherein said article is wood flooring.

11. The article coated with a radiation curable coating having antimicrobial properties as claimed in claim 8, wherein said article is furniture.

12. The article coated with a radiation curable coating having antimicrobial properties as claimed in claim 8, where said radiation curable coating is cured upon radiation with UV light.

13. The radiation curable coating as in claim 1, further comprising a chemical selected from the group consisting of diluents, plasticizers, antioxidants, colorants, solvents, emulsifiers, water, leveling agents, wetting agents, micro balloons, glass and phenolic beads, and fillers.

* * * * *